United States Patent [19]

Quinn et al.

[11] Patent Number: 4,795,430

[45] Date of Patent: Jan. 3, 1989

[54] DEVICE FOR INTUBATION OF PERCUTANEOUS ENDOSCOPIC OSTOMY

[75] Inventors: David G. Quinn, Grayslake; Robert B. Edwards, II, Libertyville; Erik Andersen, Vernon Hills, all of Ill.

[73] Assignee: Corpak, Inc., Wheeling, Ill.

[21] Appl. No.: 144,527

[22] Filed: Jan. 15, 1988

[51] Int. Cl.$^4$ .............................................. A61M 29/02
[52] U.S. Cl. ........................................... 604/97; 128/6
[58] Field of Search ....................... 604/96, 97, 98, 99; 128/4, 6

[56] References Cited

U.S. PATENT DOCUMENTS

| | | | |
|---|---|---|---|
| 3,190,291 | 6/1965 | Foley | 604/98 |
| 3,640,282 | 2/1972 | Kamen | 128/351 |
| 3,799,173 | 2/1974 | Kamen | 128/351 |
| 4,141,364 | 2/1979 | Schultze | 128/4 X |
| 4,356,824 | 11/1982 | Vazquez | 604/98 X |
| 4,666,433 | 5/1987 | Parks | 604/178 |
| 4,668,225 | 5/1987 | Russo | 604/270 |
| 4,685,901 | 8/1987 | Parks | 604/96 |

OTHER PUBLICATIONS

Gauderer and Ponsky, "A Simplified Technique for Constructing a Tube Feeding Gastrostomy", Reprint from Surgery, Gynecology & Obstetrics, Jan., 1981, vol. 152, pp. 82–85.
Gauderer and Ponsky, "Gastrostomy Without Laparotomy: A Percutaneous Endoscopic Technique", Journal of Pediatric Surgery, vol. 15, No. 6 (Dec.), 1980, pp. 872–875.
Wu, Pietrocola and Welch, "New Method of Percutaneous Gastrostomy Using Anchoring Devices", America Journal of Surgery, Am J Surg 1987; 153; pp. 230–232, Feb., 1987.

Primary Examiner—William H. Grieb
Attorney, Agent, or Firm—Wallenstein Wagner Hattis & Strampel, Ltd.

[57] ABSTRACT

A unique device for intubating an ostomy, formed by a percutaneous endoscopic technique including a multi-lumen tube, having at least a fluid delivery lumen and an inflation lumen. The tube includes a port near one end to dispose the inflation lumen to ambient air and an outlet at an other end to convey fluid from within the fluid lumen into a patient. A retention member, preferably an inflatable cuff, is joined near the other end of the tube and is inflatable and deflatable through the inflation lumen. In a deflated state, the cuff assumes an edge-free outer configuration to facilitate intubation of the device into the patient. In a fully inflated state, the cuff assumes an outer configuration defining an edged, generally flat surface to more diffusely contact and abut against inner tissue surfaces surrounding the gastrostomy. Joined to the one end of the tube is an elongated tapered sleeve which encloses the one end of the tube. The tapered end of the sleeve carries a suture loop for use in intubating the device. The sleeve includes a skirt portion which creates a circumferential air-tight seal about the tube to selectively seal the ambient air port. The skirt portion is air pressure responsive to permit escape of air from the inflation lumen through the port but preventing the ingress of air into the inflation lumen through the port.

15 Claims, 2 Drawing Sheets

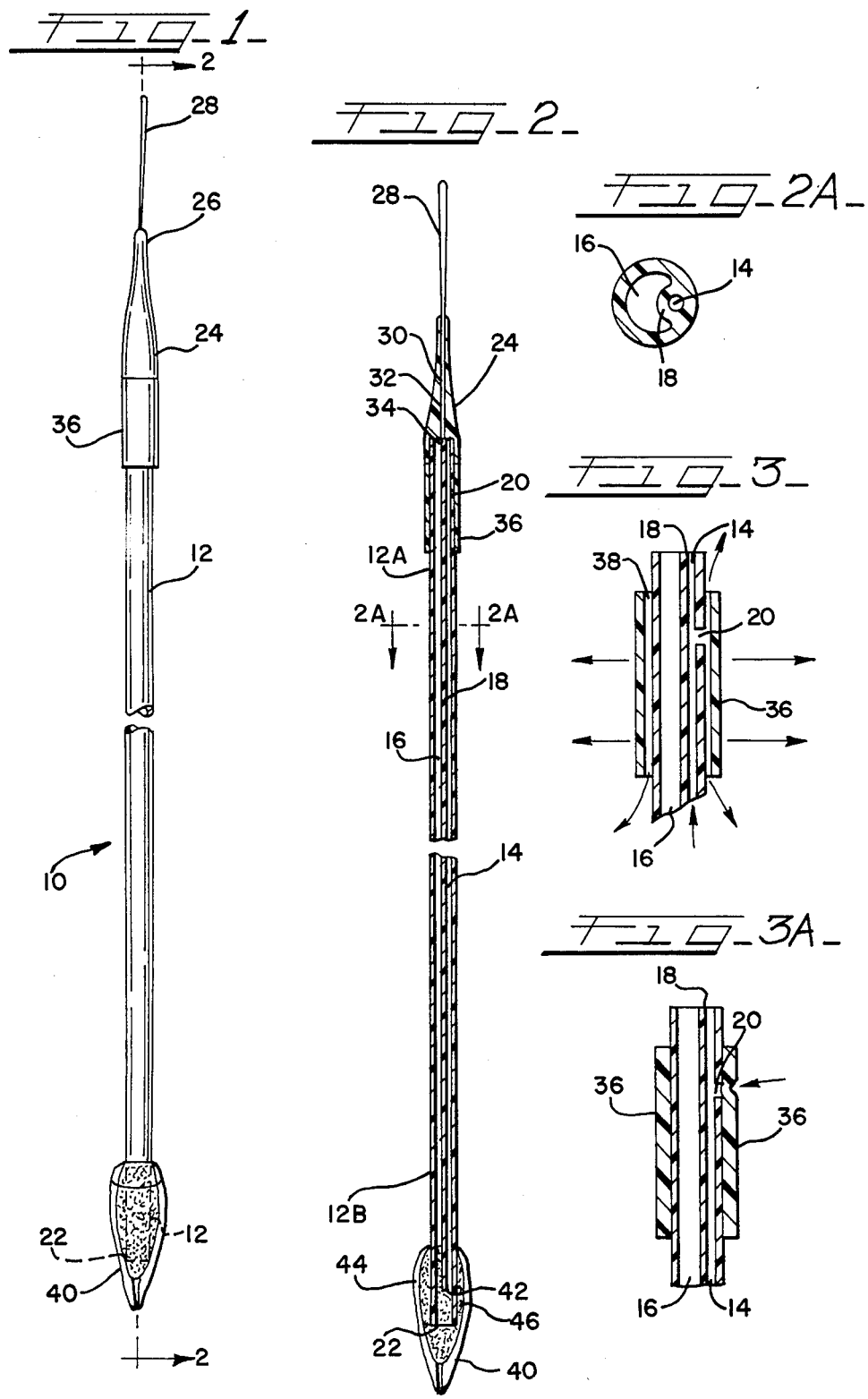

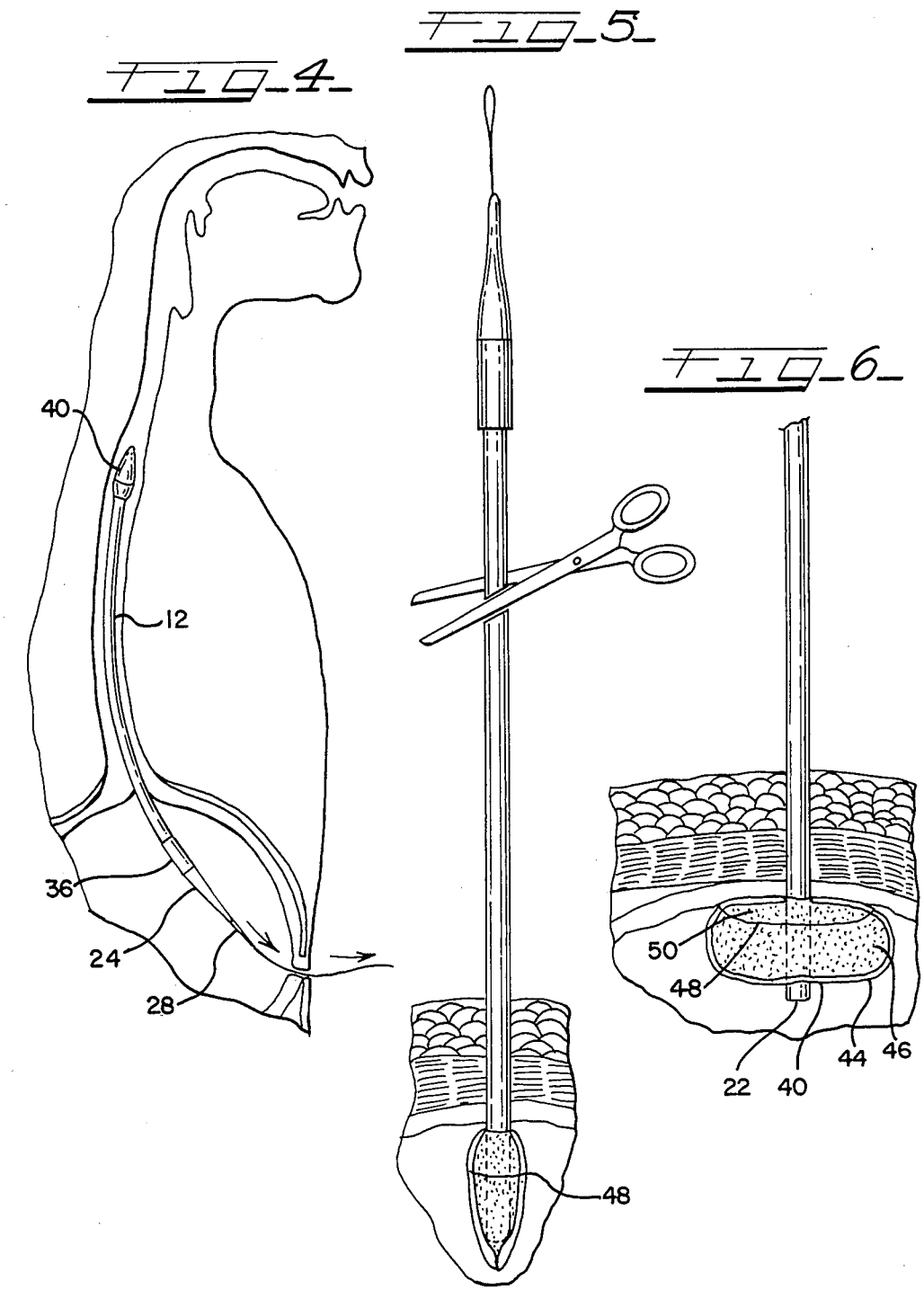

DEVICE FOR INTUBATION OF PERCUTANEOUS ENDOSCOPIC OSTOMY

TECHNICAL FIELD

The present invention generally relates to apparatuses utilized with an enteral feeding tube gastrostomy and, in particular, to a device for intubating a gastrostomy or other ostomy formed by a percutaneous endoscopic technique.

BACKGROUND ART

A surgically formed gastrostomy is a preferred method for administering enteral nutrition when oral alimentation is not possible. However the placement and formation of a gastrostomy requires a laparotomy performed under general anesthesia. Such requirements are unacceptable, particularly in patients who present a high general anesthetic risk. Hence a percutaneous endoscopic technique was developed which may be performed under local anesthesia and requires no laparotomy. This technique is disclosed of example in Gauderer & Ponsky, "A Simplified Technique For Constructing A Tube Feeding Gastrostomy", Surgery, Gynecology & Obstetrics, vol. 152, 1/81, pp. 82-85, the teachings of which are incorporated herein by reference. In addition, a percutaneous endoscopic formation of a gastrostomy may be performed by a gastroenterologist rather than a surgeon.

Generally, in forming a gastrostomy using a percutaneous endoscopic technique, an illuminating fiberoptic endoscope is inserted into a patient's mouth and advanced into the stomach. The stomach is then inflated with room air and the positioning of the endoscope may be externally visualized by the illuminated tip of the endoscope. The abdominal and gastric walls are then pierced at the positioning of the endoscope and the gastroscope thereby formed.

In order to intubate the gastrostomy, one end of a suture thread is passed externally through the gastrostomy. The one end of the suture is snared by the endoscope and drawn upward through the stomach, esophagus and out of the mouth of the patient. The suture is then tied to the end of a specially prepared catheter. The catheter is typically a 12 to 20 Fr. Pezzer or mushroom-type catheter in which a tapered cannula has been secured to one end of the catheter. The tip of the cannula carries a length of suture to permit the catheter to be tied to the one end of the suture extending from the patient's mouth. A previously removed connecting end of the Pezzer catheter is placed over the catheter and positioned slightly above the mushroom tip of the catheter to function as one perpendicular bumper for retaining the intubated catheter within the gastrostomy.

The catheter is then intubated by pulling it in a retrograde manner through the mouth, esophagus and into the stomach until the perpendicular bumper above the mushroom tip abuts against inner surfaces of the gastrostomy and the gastric wall. A second perpendicular bumper is placed over the catheter and secured to the abdominal wall to form an anchoring structure of the type disclosed in FIG. 6 of the Gauderer & Ponsky reference cited above.

There are many problems with the prior art percutaneous endoscopic catheters. The first perpendicular bumper placed above the mushroom retention tip includes several edges which result in an uncomfortable and difficult intubation of the catheter. Preferably, the retention tip should be more pliable and have a contoured, edge-free outer configuration to promote a relatively comfortable intubation of the catheter.

In addition, the prior art perpendicular bumpers which abut against the gastric and abdominal walls exert concentrated, abrasive contact pressure on specific tissue areas. Such specific contact has been found to create necrosis of the affected tissue. Hence, a need arose for an anchoring system for the retention tip of the intubated catheter which would evenly diffuse retention pressure on the surrounding affected tissue to avoid tissue necrosis.

Further, the inner perpendicular anchoring bumper in some cases would pull free and in most cases was difficult to remove upon conclusion of enteral feeding therapy. Removal is now achieved either by physically pulling the retention tip through the gastrostomy or allowing the tip to pass freely through the gastroenteral tract to become excreted. Either alternative is uncomfortable for the patient and subject to complications. Hence, a need arose for an anchoring and retention tip which could be easily and comfortably removed at the conclusion of enteral feeding therapy through the gastrostomy.

Prior to the development of the present invention, a need existed for a catheter specially designed for intubating a gastrostomy or an other ostomy formed by a percutaneous endoscopic technique having (1) an enlarged retention member which is pliable and smoothly contoured for a more comfortable intubation, (2) anchor means which more evenly distributes contact with to surrounding tissues thereby avoiding tissue necrosis, (3) anchor means which remain abutted against tissue surrounding the ostomy without pulling free and, (4) an anchor means and retention member which may be compressed or collapsed to facilitate removal of the tube externally through the gastrostomy itself upon completion of enteral feeding therapy. Preferably, unlike the prior art retention tip and bumpers, a most efficient catheter design would combine the anchor means and retention member into a single structure.

SUMMARY OF THE INVENTION

According to the present invention, a specially designed device has been developed for intubating an ostomy, as for example, a gastrostomy, formed by a percutaneous endoscopic technique. The device of the present invention meets the foregoing described needs by employing a multi-lumen enteral feeding tube, preferably having at least a fluid delivery lumen and an inflation lumen. The tube includes a port near one end to dispose the inflation lumen to ambient air and an outlet at an other end to convey fluid from within the fluid lumen into the patient. A retention member, preferably an inflatable cuff, is joined near the other end of the tube.

In the preferred embodiment of the present invention, the cuff is substantially filled with a resilient porous material for maintaining the walls of the cuff in a fully inflated position. The retention cuff is in communication with the inflation lumen and is inflatable and deflatable through the inflation lumen. The walls of the cuff are designed so that in a deflated state, the cuff assumes an edge-free, preferably rounded, outer configuration to facilitate a comfortable intubation of the device into the patient. Likewise, in a fully inflated state, the cuff assumes an outer configuration defining an edged, generally flat surface to more diffusely contact and abut against the inner tissue surfaces surrounding the gastrostomy.

Joined to the one end of the tube is an elongated tapered sleeve which encloses the one end of the tube. The tapered end of the sleeve carries, preferably, a suture loop for use in intubating the device. Preferably the sleeve includes a skirt portion which creates a circumferential air-tight seal about the tube to selectively seal the ambient air port. The skirt portion of the sleeve is air pressure responsive to permit escape of air from the inflation lumen through the port but preventing the ingress of air into the inflation lumen through the port.

The device of the present invention is utilize in intubating a gastrostomy formed by a percutaneous endoscopic technique by the following steps. First, prior to intubation of the device into a patient, the cuff is compressed, preferably by squeezing, thereby deflating the cuff and expelling air out of the inflation lumen through the port. The skirt portion of the sleeve expands outwardly in response to the greater air pressure within the lumen to permit the escape of air out of the inflation lumen through the port. Upon fully deflating the retention cuff, the air pressure within the inflation lumen decreases relative to ambient air pressure such that the skirt portion contracts inwardly to seal the ambient air port thus preventing ingress of air into the inflation lumen. Sealing of the ambient air port prevents re-inflation of the cuff. In a deflated state, the retention cuff assumes an edge free generally oval outer configuration.

Next, the suture loop carried on the tapered end of the sleeve is tied to the one end of the suture which extends from the patient's mouth. The gastroenterologist then begins pulling on the other end of the suture extending externally from the gastrostomy to lead the device in a retrograde manner through the mouth, esophagus and ultimately into the stomach. The retrograde drawing of the device continues until the deflated cuff abuts against inner tissue surfaces surrounding the gastrostomy. Air is then externally introduced into the inflation lumen to reinflate the retention cuff to change the outer configuration of the cuff to create the generally flat anchor surface. The inflation lumen is then sealed with a plug or other means to prevent inadvertent deflation of the cuff.

In the preferred method of practicing the present invention, the gastroenterologist may sever an external length of the multi-lumen tube to remove the enclosed sleeve from the tube and expose the inflation lumen to ambient air resulting in re-inflation of the cuff. The inflation lumen should be sealed with a plug or other device to prevent deflation of the retention cuff. A luer adaptor or other tube connecting device may be affixed to the severed end of the tube and to place the tube in fluid communication with an enteral nutritional fluid source.

Other advantages and aspects of the invention will become apparent upon making reference to the specification, claims, and drawings to follow.

BRIEF DESCRIPTION OF DRAWINGS

FIG. 1 discloses in perspective view a preferred embodiment of the present invention;

FIG. 2 is a longitudinal section taken along line 2—2 in FIG. 1;

FIG. 2A is a vertical section taken through line 2A—2A of FIG. 2;

FIG. 3 is a fragmented detailed view of a portion of FIG. 2 disclosing outward flexing of the preferred skirt portion of the elongated sleeve permitting an escape of air from within the inflation lumen;

FIG. 3A is the same view of FIG. 3 disclosing an inward contraction of the skirt portion to seal the ambient air port of the inflation lumen;

FIG. 4 illustrates retrograde intubation of a preferred embodiment of the device of the present invention;

FIG. 5 illustrates severing a portion of the tube of the present invention to introduce air into the inflation lumen; and, FIG. 6 discloses a preferred outer configuration of a fully inflated retention cuff of the present invention.

DETAILED DESCRIPTION

While this invention is susceptible of embodiment in many different forms, there is shown in the drawings and will herein be described in detail a preferred embodiment of the invention. The present disclosure is to be considered as an exemplification of the principles of the invention and is not intended to limit the broad aspect of the invention to embodiment illustrated.

Referring now to the drawings, FIG. 1 discloses a preferred embodiment of device 10 of the present invention comprised of a multi-lumen enteral feeding tube. As disclosed in FIG. 2 and best disclosed in FIG. 2A, feeding tube 12 includes at least an inflation lumen 14 and a fluid delivery lumen 16. Lumens 14 and 16 are separated by a septum 18. As disclosed in FIG. 2, one end 12A of tube 12 has at least one ambient air port 20 which as will be disclosed later in greater detail, disposes inflation lumen 14 in communication with ambient air. At an other end 12B of tube 12, the fluid outlet 22 (shown in phantom in FIG. 2) conveys fluid from fluid lumen 16 into a patient.

Sealably secured to end 12A of tube 12 is an enclosed sleeve 24, preferably having a tapered elongated conical terminal end 26. The tapered conical outer configuration of terminal end 26 permits atraumatic parting of esophageal and gastric tissues during the intubation process. As disclosed in FIGS. 1 and 2 disposed on the terminal end 26 of sleeve 24 is a suture loop 28 which permits device 10 to be tied to the end of the suture extending from the patient's mouth during the percutaneous endoscopic technique (not shown in the drawings). As disclosed in FIG. 2, suture loop 28 may preferably fully extend through sleeve 24 through a channel 32 and be secured to end 12A of tube 12 by a fastening knot or other fastening device 34 secured to the septum 18.

Joined to sleeve 24 is a skirt portion 36 which circumferentially surrounds end 12A of tube 12 in such a manner to create an airtight seal between skirt portion 36 and outer surfaces of end 12A. Skirt portion 36 is made from a highly pliable plastic or latex rubber so as to be air pressure responsive permitting selective sealing of ambient air port 20. Specifically, skirt portion 36 responds to greater air pressure within inflation lumen 14 to permit the escape of air out of lumen 14 through port 20. However, when ambient air pressure exceeds the air pressure within lumen 14, then skirt portion 36 contracts inwardly to seal port 20 to prevent the further ingress of air into lumen 14.

FIGS. 3 and 3A disclose in greater detail the selective sealing or diaphragmatic action of skirt portion 36. As disclosed in FIG. 3, when air pressure within inflation lumen 14 increases to exceed ambient air pressure, skirt 36 expands outwardly away from the walls of tube 12 to define a circumferential gap 38 which permits air to exit ambient port 20 and escape from under skirt portion 36. As disclosed in FIG. 3A, when ambient air pressure exceeds the air pressure within inflation lumen 14, skirt portion 36 contracts circumferentially about tube 12 closing gap 38 and thereby forming an airtight seal about tube 12 and port 20.

The selective sealing of ambient port 20 allows for the controlled inflation and deflation of a retention/anchor member, which preferably is embodied as an annular cuff 40. As best disclosed in FIG. 2, retention cuff 40 is affixed to the other end 12B of tube 12. Retention cuff 40 is sealed and in gas communication with inflation lumen 14 through a terminal opening 42 in tube 12. As shown in phantom in FIGS. 1 and 2, tube 12 passes through cuff 40 so that, as disclosed in FIG. 6, fluid outlet 22 extends below cuff 40. In the preferred embodiment of the present invention, cuff 40 is comprised of a distendable outer wall 40 which defines a cavity preferably substantially filled with a porous resilient foam material 46. As disclosed in FIG. 6, foam material 46 is cut in a configuration so that when cuff 40 is in a fully expanded position, foam material 46 maintains walls 44 in expanded position.

Retention cuff 40 is placed in a deflated state by compressing, preferably by squeezing, cuff 40 so that the air trapped within walls 44 and foam material 46 is expelled upwardly into the inflation lumen and out of port 20. Discontinuing such squeezing of cuff 40 results in a decrease in air pressure within inflation lumen 14 so that ambient air pressure acts upon skirt 36 to seal port 20 in the manner described above. Such sealing of port 20 prevents reinflation of retention cuff 40 and maintains cuff 40 in a deflated position. Reinflation of cuff 40 is achieved by introducing ambient air into inflation lumen 14 by methods to be described below in greater detail.

Cuff 40 combines in a single structure both the retention and anchoring functions achieved by prior art catheter mushroom-type tips and perpendicular rubber bumpers. However, unlike the prior art mushroom tip/bumper combination, cuff 40 in a deflated state, assumes an essentially end-free, rounded configuration which facilitates intubation of device 10. Cuff 40, in a deflated state, preferably assumes a oval or pill-shape as disclosed in FIGS. 1 and 2. In a fully inflated state, cuff 40 assumes a different configuration. The walls 44 of cuff 40 are molded or pre-formed so that the outer configuration of cuff 40 changes from a deflated state to a fully inflated state. For example, cuff 40 includes a fold or crease line 48 which changes the outer configuration of cuff 40 from deflation to full inflation. As disclosed in FIG. 6, upon full inflation of cuff 40, fold line 48 defines a peripheral edge of a generally flat retention and anchor surface 50. Surface 50 is of a sufficient surface area to evenly distribute contact pressures on the tissue surrounding the gastrostomy to avoid the necrosis of tissue commonly encountered by use of prior art retention bumpers. Hence, a novel aspect of the present invention is that the retention cuff, in a deflated position, has an edge-free contour to facilitate a comfortable intubation, whereas, in a fully inflated state, retention cuff 40 assumes a different configuration to define an edged, flattened surface for anchoring tube 12 within the gastrostomy.

FIGS. 4 through 6 disclose the general method of using device 10 in intubating an ostomy formed by a percutaneous endoscopic technique. As disclosed in FIG. 44, after the length of suture has been drawn out of a patient's mouth such that the free ends of the suture extend from both the patient's mouth and the gastrostomy, the suture is tied to loop 28 of the device of the present invention. The device of the present invention is then drawn downward through the mouth, esophagus and into the stomach in a retrograde manner. The pulling of the suture through the gastrostomy continues until the deflated retention cuff 40 abuts against the inner tissue surfaces of the gastrostomy as disclosed in FIG. 5. To retain and anchor the fluid outlet end 12B of tube 12 within the gastrostomy, retention cuff 40 is re-inflated by introducing air into the inflation lumen 14. In a preferred method of using the present invention, this may be accomplished by severing, as disclosed in FIG. 5, completely through a portion of tube 12 external to the gastrostomy. Upon severing completely through tube 12, inflation lumen 14 is exposed to ambient air thereby raising the air pressure within lumen 14 to automatically inflate cuff 40. In some instances it may be necessary to assist the inflation operation by injection air into inflation lumen 14 through the insertion of the tip of an air-filled syringe into inflation lumen 14. Upon full inflation of retention cuff 40, inflation lumen 14 is sealed with a plug or other device to prevent deflation of cuff 40. Retention and anchoring of device 10 is complete and a luer adaptor or other tube connection means may be affixed to the severed end of tube 12 to join tube 12 to a source of enteral nutritional fluid. Such adaptor or tube connection means may also function to seal inflation lumen 14.

While the specific embodiments have been illustrated and described, numerous modifications come to mind without significantly departing from the spirit of the invention and the scope of protection is only limited by the scope of the accompanying

We claim:

1. A device for intubating an ostomy, such as a gastrostomy, formed by a percutaneous endoscopic technique, comprising:

a tube having at least a fluid lumen and an inflation lumen, the tube having a port near one end to dispose the inflation lumen to ambient air and an outlet at an other end to convey fluid from within the fluid lumen into the patient;

a retention member joined near the other end of the tube, the member being inflatable through the inflation lumen, the member in a deflated state having a generally edge-free outer configuration to facilitate intubation, the member in an inflated state defining at least one edged and generally flat retention and anchoring surface;

an elongated sleeve joined to and enclosing the one end of the tube, the sleeve being edge-free to define an edge-free outer configuration for gently parting gastroenteral tissues during intubation;

means for sealing selectively the ambient air port of the tube, the sealing means permitting escape of air from the inflation lumen through the port but preventing ingress of air into the inflation lumen;

wherein prior to intubation of the device into a patient the retention member is compressed to deflate the member by expelling air out of the inflation lumen through the port, the sealing means seals the port to prevent re-inflation of the member, the one end of the tube is drawn through the patient in a retrograde manner until the deflated retention member abuts against inner tissue surfaces of the gastrostomy, air is introduced into the inflation lumen to re-inflate the member and anchor the device against the inner tissue surfaces of the gastrostomy, and the inflation lumen is sealed to prevent deflation of the retention member.

2. The device of claim 1 wherein the means for selectively sealing the port includes:

a skirt portion joined to the sleeve, the skirt portion forming an air-tight seal about the circumference of the tube, the skirt portion expanding outwardly in response to greater air pressure within the inflation lumen to permit expulsion of air out of the port and contracting inwardly in response to greater air pressures outside the inflation lumen to seal the port.

3. The device of claim 1 wherein the inflatable retention member includes a substantially foam filled annular cuff.

4. The device of claim 3 wherein the annular cuff has at least one generally flattened surface for abutment against the inner surfaces of the gastrostomy.

5. The device of claim 1 wherein a loop of suture is carried on a terminal end of the sleeve to draw the device in a retrograde manner through the esophagus and the gastrostomy.

6. The device of claim 5 wherein the terminal end of the sleeve has a conical shape.

7. In a method for intubating an ostomy formed by a percutaneous endoscopic technique, the technique including inserting a fiberoptic endoscope into a patient's mouth, advancing the endoscope into the patient to illuminate and externally visualize a desired endoscope positioning, forming the ostomy through abdominal and gastric walls of the patient at the desired endoscope positioning, and passing one end of a suture externally through the ostomy and drawing the one end of the suture up through and out of the patient's mouth, an other end of the suture remaining outside the gastrostomy, the improvement comprising the steps of:

tying the suture to one end of a tube having at least an inflation lumen and a fluid lumen, the tube having a port near the one end to dispose the inflation lumen to ambient air and an outlet at an other end to convey fluid from the fluid lumen into the patient, an enclosed elongated sleeve joined to the one end of the tube, the sleeve having means for selectively sealing the port to permit escape of air from the inflation lumen but preventing ingress of air into the inflation lumen;

deflating an inflatable retention member joined near the other end of the tube, the member being inflatable through the inflation lumen, the means for sealing the port preventing re-inflation of the member;

intubating the tube by pulling on the other end of the suture to draw and lead the one end of the tube in a retrograde manner through the patient until the retention member abuts against inner tissue surfaces of the ostomy; and, inflating the retention member to anchor the member against the inner tissue surfaces of the ostomy.

8. The method of claim 7 wherein the step of deflating the retention member includes:

compressing a foam-filled inflatable retention cuff until air is expelled out of the cuff and the inflation lumen.

9. The method of claim 7 wherein the step of inflating the retention member includes:

introducing ambient air into the inflation lumen.

10. The method of claim 9 wherein the step of introducing air into the inflation lumen includes:

severing the tube externally to the ostomy to expose the inflation lumen to ambient air.

11. The method of claim 10 wherein after the step of severing the tube, further including the step of:

joining a tube connector device to the severed end of the tube.

12. The method of claim 7 wherein the step of tying the suture to the one end of the tube includes:

tying the suture to a suture loop carried from a terminal end of the enclosed sleeve.

13. The method of claim 7 wherein after the step of inflating the retention member, further including the step of:

sealing the inflation lumen to prevent the retention member from deflating.

14. The method of claim 7 wherein the ostomy includes a gastrostomy.

15. The method of claim 7 wherein the ostomy includes a cystostomy.

* * * * *

UNITED STATES PATENT AND TRADEMARK OFFICE
CERTIFICATE OF CORRECTION

PATENT NO. : 4,795,430
DATED : January 3, 1989
INVENTOR(S) : David G. Quinn, Robert B. Edwards II, Erik Andersen It is certified that error appears in the above-identified patent and that said Letters Patent is hereby corrected as shown below:

In the Specification:

In Column 3, line 14, delete "utilize" and insert --utilized--

In Column 6, line 21, delete "injection" and insert --injecting--

In Column 6, line 36, after the word "accompanying" insert --Claims.--

Signed and Sealed this

Twenty-third Day of May, 1989

Attest:

DONALD J. QUIGG

*Attesting Officer*  *Commissioner of Patents and Trademarks*